(12) United States Patent
Roh et al.

(10) Patent No.: US 12,093,105 B2
(45) Date of Patent: Sep. 17, 2024

(54) WALKING ASSISTANCE DEVICE AND CONTROL METHOD OF WALKING ASSISTANCE DEVICE

(71) Applicant: Samsung Electronics Co., Ltd., Suwon-si (KR)

(72) Inventors: Changhyun Roh, Suwon-si (KR); Younbaek Lee, Suwon-si (KR); Jongwon Lee, Suwon-si (KR); Bokman Lim, Suwon-si (KR)

(73) Assignee: Samsung Electronics Co., Ltd., Gyeonggi-do (KR)

( * ) Notice: Subject to any disclaimer, the term of this patent is extended or adjusted under 35 U.S.C. 154(b) by 947 days.

(21) Appl. No.: 16/991,649

(22) Filed: Aug. 12, 2020

(65) Prior Publication Data
US 2021/0085554 A1 Mar. 25, 2021

(30) Foreign Application Priority Data
Sep. 24, 2019 (KR) .................. 10-2019-0117660

(51) Int. Cl.
*G06F 1/3212* (2019.01)
*A61B 5/11* (2006.01)
(Continued)

(52) U.S. Cl.
CPC ............ *G06F 1/3212* (2013.01); *A61B 5/112* (2013.01); *A61H 3/008* (2013.01); *G06F 1/3296* (2013.01);
(Continued)

(58) Field of Classification Search
CPC ..... A61B 5/112; A61B 5/6811; A61B 5/6828; A61H 3/008; A61H 1/0262; A61H 2003/007; A61H 2201/1207; A61H 2201/165; A61H 2201/1628; A61H 2201/5007; A61H 2203/0406;
(Continued)

(56) References Cited

U.S. PATENT DOCUMENTS

2010/0049333 A1* 2/2010 Endo ................. A61H 3/00
602/5
2010/0130894 A1 5/2010 Ikeuchi
(Continued)

FOREIGN PATENT DOCUMENTS

JP 2004-329520 A 11/2004
JP 2009197514 A * 9/2009 ............. Y02E 60/10
(Continued)

OTHER PUBLICATIONS

Notice of Preliminary Rejection issued Jun. 17, 2024 in Korean Application No. 10-2019-0117660.

*Primary Examiner* — Dale Moyer
(74) *Attorney, Agent, or Firm* — Harness, Dickey & Pierce, P.L.C.

(57) ABSTRACT

A control method of a walking assistance apparatus is disclosed. The control method of the walking assistance apparatus includes estimating an operable time of the walking assistance apparatus based on an amount of remaining power and power consumption of the walking assistance apparatus, determining whether the operable time satisfies a preset criterion, and generating a torque profile based on an algorithm of a power saving mode when the preset criterion is satisfied.

17 Claims, 9 Drawing Sheets

(51) Int. Cl.
    *A61H 3/00*          (2006.01)
    *G06F 1/3296*      (2019.01)

(52) U.S. Cl.
    CPC ............... *A61H 2003/007* (2013.01); *A61H 2201/1207* (2013.01); *A61H 2201/1628* (2013.01); *A61H 2201/5007* (2013.01); *A61H 2203/0406* (2013.01); *A61H 2205/088* (2013.01)

(58) Field of Classification Search
    CPC ... A61H 2205/088; G06F 1/325; G06F 3/011; G06F 3/016; G06F 1/3296; G06F 1/3212; B25J 9/0006; G05B 2219/40305; Y02E 60/10
    See application file for complete search history.

(56) References Cited

U.S. PATENT DOCUMENTS

| | | |
|---|---|---|
| 2013/0053736 A1 | 2/2013 | Konishi |
| 2013/0102934 A1 | 4/2013 | Ikeuchi |
| 2019/0105777 A1 | 4/2019 | Dalley et al. |
| 2021/0378903 A1* | 12/2021 | Mooney .................. A61H 3/00 |

FOREIGN PATENT DOCUMENTS

| | | | | |
|---|---|---|---|---|
| JP | 2009197515 A | * | 9/2009 | |
| JP | 2012200318 A | * | 10/2012 | |
| JP | 2016005498 A | * | 1/2016 | |
| KR | 10-2015-0033505 A | | 4/2015 | |
| KR | 10-2017-0019175 A | | 2/2017 | |
| KR | 10-2018-0136656 A | | 12/2018 | |
| WO | WO-2015181996 A1 | * | 12/2015 | ............... A61H 3/04 |

* cited by examiner

WALKING ASSISTANCE DEVICE AND CONTROL METHOD OF WALKING ASSISTANCE DEVICE

CROSS-REFERENCE TO RELATED APPLICATION

This application claims priority under 35 U.S.C. § 119 to Korean Patent Application No. 10-2019-0117660 filed on Sep. 24, 2019, in the Korean Intellectual Property Office, the entire contents of which are incorporated herein by reference in their entirety.

BACKGROUND

1. Field

At least one example embodiment relates to a walking assistance apparatus and/or a method for controlling the walking assistance apparatus.

2. Description of the Related Art

With the onset of rapidly aging societies, there may be an increase in the number of people experiencing inconvenience and/or pain from joint problems. Thus, there is a growing interest in walking assistance apparatuses enabling the elderly and/or patients having joint problems to walk with less effort. Furthermore, walking assistance apparatuses increasing muscular strength of human bodies are desired for military purposes.

In general, walking assistance apparatuses for assisting motion of lower parts of bodies may include body frames disposed on trunks of users, pelvic frames coupled to lower sides of the body frames to cover pelvises of the users, femoral frames disposed on thighs of the users, sural frames disposed on calves of the users, and/or pedial frames disposed on feet of the users. The pelvic frames and femoral frames may be connected rotatably by hip joint portions, the femoral frames and sural frames may be connected rotatably by knee joint portions, and/or the sural frames and pedial frames may be connected rotatably by ankle joint portions.

The walking assistance apparatus is attached to a body of a user to move along with the user and thus, may be designed to be portable. To achieve increased portability, the walking assistance apparatus may receive power through a battery mounted therein, where a supply of the power from the battery may be limited.

SUMMARY

Some example embodiments relate to a control method of a walking assistance apparatus.

In some example embodiments, the control method includes estimating an operable time of the walking assistance apparatus based on an amount of remaining power and a power consumption of the walking assistance apparatus; and generating a torque profile based on an algorithm of a power saving mode in response to the operable time satisfying a set criterion.

In some example embodiments, the generating of the torque profile includes setting the torque profile such that a maximum intensity of a torque applied to a driver of the walking assistance apparatus in the power saving mode is less than a maximum intensity of a torque applied to the driver in a normal mode.

In some example embodiments, the generating of the torque profile includes setting the torque profile based on a set torque profile associated with the power saving mode.

In some example embodiments, the generating of the torque profile includes setting, in the power saving mode, the torque profile such that a maximum intensity of a torque applied to a driver of the walking assistance apparatus to assist a leg lifting motion of a user wearing the walking assistance apparatus is greater than a maximum intensity of a torque applied to the driver to assist a leg lowering motion of the user.

In some example embodiments, the estimating of the operable time includes calculating the amount of remaining power; and estimating the power consumption.

In some example embodiments, the generating of the torque profile includes measuring a current gait motion of a user; defining a state variable based on the current gait motion; and generating, based on the state variable and a gravity, the torque profile for a descending state of a swing phase of one or more of a left leg or right leg of the user.

In some example embodiments, the generating of the torque profile includes generating the torque profile such that the torque profile compensates for a frictional force of the left leg or the right leg of the descending state of the swing phase based on the gravity.

In some example embodiments, the control method further includes informing a user wearing the walking assistance apparatus of a change to the power saving mode in response to the set criterion being satisfied.

In some example embodiments, the informing includes informing the user of the change to the power saving mode through a display or a speaker.

In some example embodiments, the control method further includes driving a driver of the walking assistance apparatus based on the torque profile.

Some example embodiments relate to a non-transitory computer-readable medium including computer readable instructions that, when executed, cause a computer to perform the control method.

Some example embodiments relate to a walking assistance apparatus.

In some example embodiments, the walking assistance apparatus includes a sensor configured to measure a gait motion of a user wearing the walking assistance apparatus; and a controller configured to, estimate an operable time of the walking assistance apparatus based on an amount of remaining power and power consumption of the walking assistance apparatus, and generate a torque profile based on an algorithm of a power saving mode in response to the operable time satisfying a set criterion.

In some example embodiments, the controller is configured to set the torque profile such that a maximum intensity of a torque applied to a driver in the power saving mode is less than a maximum intensity of a torque applied to the driver in a normal mode.

In some example embodiments, the controller is configured to set the torque profile based on a set torque profile associated with the power saving mode.

In some example embodiments, the controller is configured to set, in the power saving mode, the torque profile such that a maximum intensity of a torque applied to a driver to assist a leg lifting motion of the user is greater than a maximum intensity of a torque applied to the driver to assist a leg lowering motion of the user.

In some example embodiments, the walking assistance apparatus further includes at least one of a display and a speaker configured to inform the user of a change to the power saving mode when the operable time satisfies the set criterion.

In some example embodiments, the walking assistance apparatus further includes a driver configured to drive a support of the walking assistance apparatus based on the torque profile to assist the gait motion of the user.

Additional aspects of example embodiments will be set forth in part in the description which follows and, in part, will be apparent from the description, or may be learned by practice of the disclosure.

BRIEF DESCRIPTION OF THE DRAWINGS

These and/or other aspects will become apparent and more readily appreciated from the following description of example embodiments, taken in conjunction with the accompanying drawings of which.

DETAILED DESCRIPTION

Figure 1:
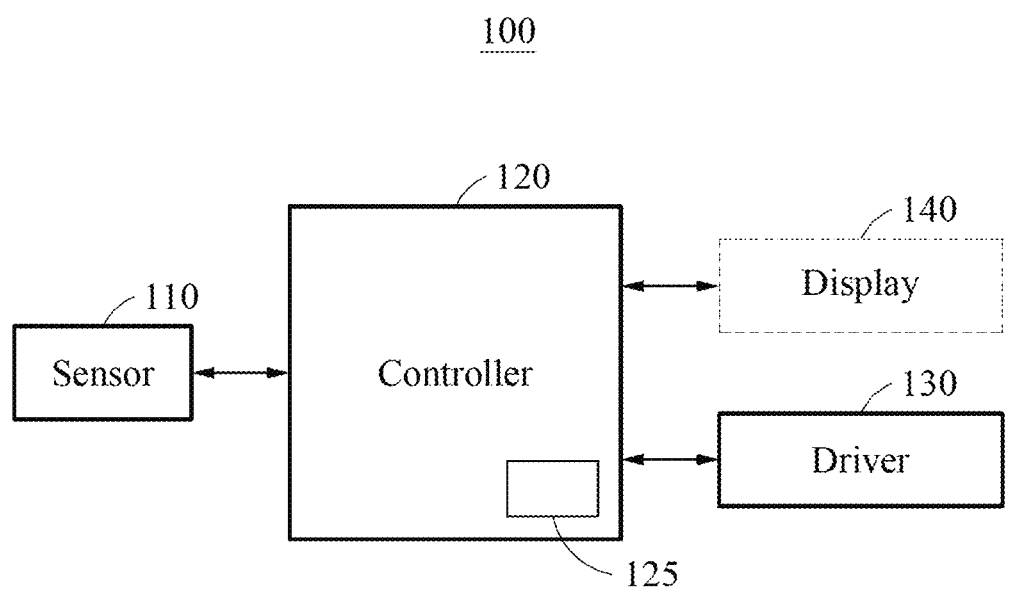
FIG. 1 is a block diagram illustrating a walking assistance apparatus according to at least one example embodiment.

Hereinafter, some example embodiments will be described in detail with reference to the accompanying drawings. Regarding the reference numerals assigned to the elements in the drawings, it should be noted that the same elements will be designated by the same reference numerals, wherever possible, even though they are shown in different drawings. Also, in the description of embodiments, detailed description of well-known related structures or functions will be omitted when it is deemed that such description will cause ambiguous interpretation of the present disclosure.

It should be understood, however, that there is no intent to limit this disclosure to the particular example embodiments disclosed. On the contrary, example embodiments are to cover all modifications, equivalents, and alternatives falling within the scope of the example embodiments. Like numbers refer to like elements throughout the description of the figures.

In addition, terms such as first, second, A, B, (a), (b), and the like may be used herein to describe components. Each of these terminologies is not used to define an essence, order or sequence of a corresponding component but used merely to distinguish the corresponding component from other component(s). It should be noted that if it is described in the specification that one component is "connected", "coupled", or "joined" to another component, a third component may be "connected", "coupled", and "joined" between the first and second components, although the first component may be directly connected, coupled or joined to the second component.

The terminology used herein is for the purpose of describing particular embodiments only and is not intended to be limiting. As used herein, the singular forms "a," "an," and "the," are intended to include the plural forms as well, unless the context clearly indicates otherwise. It will be further understood that the terms "comprises," "comprising," "includes," and/or "including," when used herein, specify the presence of stated features, integers, steps, operations, elements, and/or components, but do not preclude the presence or addition of one or more other features, integers, steps, operations, elements, components, and/or groups thereof.

It should also be noted that in some alternative implementations, the functions/acts noted may occur out of the order noted in the figures. For example, two figures shown in succession may in fact be executed substantially concurrently or may sometimes be executed in the reverse order, depending upon the functionality/acts involved.

Various example embodiments will now be described more fully with reference to the accompanying drawings in which some example embodiments are shown. In the drawings, the thicknesses of layers and regions are exaggerated for clarity.

Figure 2:
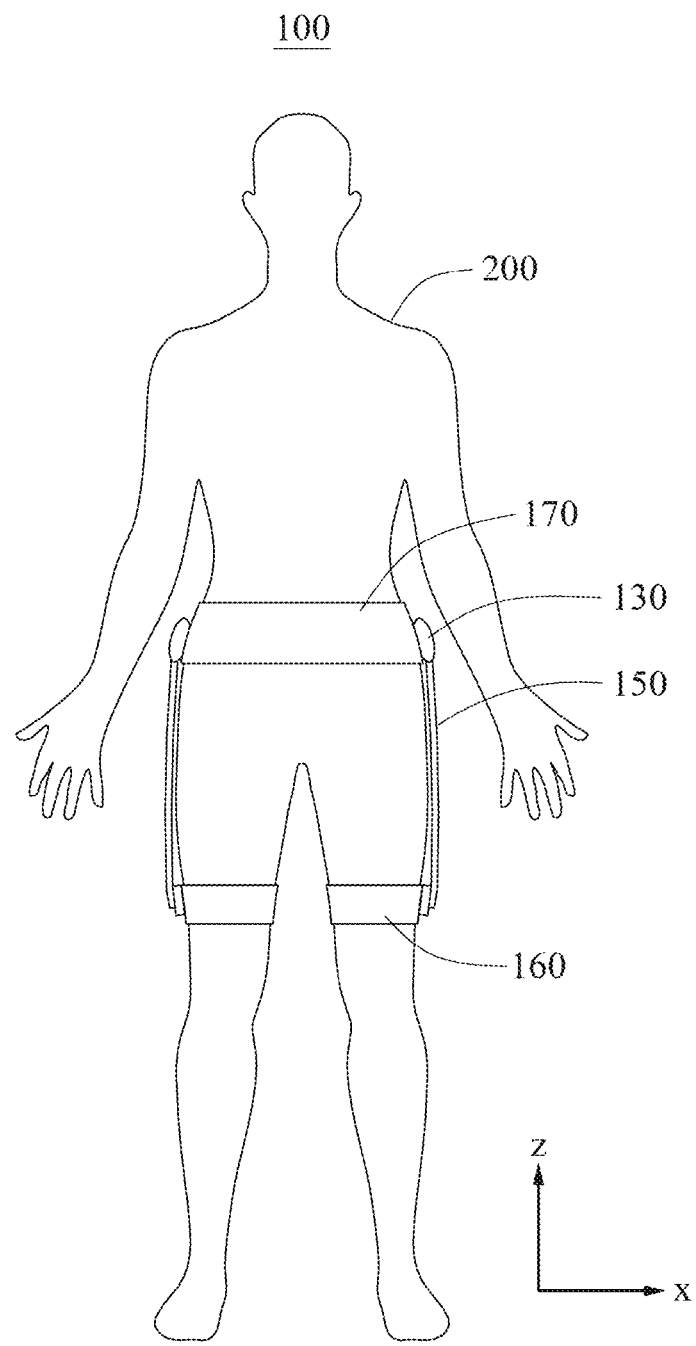
FIG. 2 is a front view illustrating a target body wearing the walking assistance apparatus of FIG. 1.

FIG. 1 is a block diagram illustrating a walking assistance apparatus according to at least one example embodiment and FIG. 2 is a front view illustrating a target body wearing the walking assistance apparatus of FIG. 1.

Referring to FIGS. 1 and 2, a walking assistance apparatus (gait assist device or walking assist device, WAD) 100 may be a device for performing a function of assisting a gait of a user (or wearer) 200 wearing the walking assistance apparatus 100. When the walking assistance apparatus 100 performs a gait assistance function, the walking assistance apparatus 100 may assist a portion of or whole leg of the user 200 to assist a gait of user 200. For example, when a normal person or an elderly person wears the walking assistance apparatus 100, the walking assistance apparatus 100 may allow walking for a long time to expand a walking ability of the user 200 or improve an abnormal gait motion of a pedestrian. Also, the walking assistance apparatus 100 may enable independent walking by assisting a force required for walking.

The walking assistance apparatus 100 may be, for example, a wearable device and include a battery (not shown). Since the battery has a limited amount of power, an operable time of the walking assistance apparatus may also be limited. Therefore, in one or more example embodiments, the walking assistance apparatus 100 may implement a control method that delays an assist-off time of the walking assistance apparatus 100 when an insufficient amount of power remains in the battery during an operation of the walking assistance apparatus 100. For example, when a sufficient amount of power is supplied, the walking assistance apparatus 100 may operate in a normal mode in which a separate control operation for reducing power consumption is not performed. In this example, when the amount of power is reduced to be less than a set (or, alternatively, a preset) value, the walking assistance apparatus 100 may operate in a power saving mode to increase (or, alternatively, maximize) the operable time.

In the power saving mode, the walking assistance apparatus 100 may be controlled to reduce the power consumption in the walking assistance apparatus 100. The walking assistance apparatus 100 may be controlled to reduce the power consumption based on an amount of remaining power. The walking assistance apparatus 100 may estimate an operable time based on the amount of remaining power and switch to the power saving mode to reduce the power consumption to prolong the operable time. The walking assistance apparatus 100 may operate in the power saving mode to save power in contrast to the normal mode in which the power consumption is not restricted.

Referring to FIGS. 1 and 2, the walking assistance apparatus 100 may include a sensor 110, a controller 120, and a driver 130. In some example embodiments, the walking assistance apparatus 100 may further include a display 140, a speaker (not shown), an assistance torque transmitting member 150, a supporting member 160, and a fixing member 170.

Although FIG. 2 illustrates the walking assistance apparatus 100 as, for example, a hip-type walking assistance apparatus, operating on a thigh of the user 200, the type of the walking assistance apparatus 100 is not limited thereto. The walking assistance apparatus 100 may assist a motion of another part of an upper body, for example, a hand, an upper arm, or a lower arm of the user, or a motion of another part of a lower body, for example, a foot, or a calf of the user. The walking assistance apparatus 100 may be applicable to, for example, a walking assistance apparatus that supports an entire pelvic limb, a walking assistance apparatus that supports a portion of a pelvic limb, and the like. The walking assistance apparatus that supports a portion of a pelvic limb may be applicable to, for example, a walking assistance apparatus that supports up to a knee, or a walking assistance apparatus that supports up to an ankle.

The sensor 110 may measure a current gait motion of the user 200. The current gait motion of the user 200 may be measured by sensing joint positions of both legs of the user 200. For example, the sensor 110 may measure both hip-joint angle information corresponding to the joint positions. As illustrated in FIG. 2, the sensor 110 may be implemented in at least one of the driver 130, the fixing member 150, and the supporting member 160.

The both hip-joint angle information may include at least one of both hip-joint angles, a difference between the both hip-joint angles, moving directions of both hip-joints, and both hip-joint angular velocity information. The sensor 110 may be implemented as, for example, a hall sensor. The sensor 110 may wired or wirelessly transmit the both hip-joint angle information to the controller 120.

The controller 120 may control an overall operation of the walking assistance apparatus 100. For example, the controller 120 may control the driver 130 to output a force for assisting a gait of the user 200. The power may indicate an extension or flexion force to push or pull the leg of the user 200. The power may be, for example, an assistance torque.

The controller 120 may be implemented in processing circuitry such as hardware including logic circuits; a hardware/software combination such as a processor executing software; or a combination thereof and memory. For example, the processing circuitry more specifically may include, but is not limited to, a central processing unit (CPU), an arithmetic logic unit (ALU), a digital signal processor, a microcomputer, a field programmable gate array (FPGA), a programmable logic unit, a microprocessor, application-specific integrated circuit (ASIC), etc. The controller 120 may execute software loaded in the memory 125 that configures the controller 120 as a special purpose computer to increase (or, alternatively, maximize) an operable time of the walking assistance apparatus 100 by reducing power consumption thereof by switching from a normal operation mode to a power savings mode, when the amount of power is less than a set (or, alternatively, a preset) value. Therefore, the special purpose processing circuitry improves the performing the walking assistance apparatus 100 itself.

The controller 120 may define a state variable based on the current gait motion of the user 200 received from the sensor 110, which may also be expressed as that the controller 120 defines a state variable by receiving a feedback about the current gait motion of the user 200. The state variable may include a gain related to an intensity of torque, an influence exerted by the gravity on the walking assistance apparatus 100, and a delay related to a torque output time. The controller 120 may generate a torque profile based on the state variable.

The controller 120 may control the driver 130 to initiate a gait assistance based on a torque profile. In this example, the controller 120 may initiate outputting of the torque profile to assist walking of the user 200. Also, the controller 120 may control the driver 130 to terminate the gait assistance. In this example, the controller 120 may terminate outputting the torque profile.

The controller 120 may estimate an operable time of the walking assistance apparatus 100 based on an amount of power remaining in the battery that supplies power to the walking assistance apparatus 100, and power consumption of the walking assistance apparatus 100. For example, an intensity of torque applied to the driver 130 may correspond to an intensity of voltage or current supplied to the driver. Also, the power consumption of the walking assistance apparatus 100 may be estimated based on a current effective value (current root mean square (RMS) value) or a voltage effective value (voltage RMS value) for a predetermined period of time. The controller 120 may estimate the operable time of the walking assistance apparatus 100 based on the estimated power consumption and an amount of power remaining in the battery embedded in the walking assistance apparatus 100. For example, the operable time may be estimated by dividing the amount of power remaining in the battery by the estimated power consumption of the walking assistance apparatus 100.

The controller 120 may control an assistance torque output by the driver 130 to the user 200 based on the torque profile of the power saving mode. The controller 120 may reduce the power consumption by controlling the assistance torque based on a torque profile determined using an algorithm of the power saving mode. When the operable time of the walking assistance apparatus 100 satisfies a set (or, alternatively, a preset) criterion, the controller 120 may generate a torque profile using the algorithm of the power saving mode.

For example, when the operable time is less than 30 minutes, the controller 120 may start a process for operating in the power saving mode from the normal mode. Here, the normal mode may be a mode of the walking assistance apparatus 100 operating when a sufficient amount of power remains in the battery and the operable time is greater than a set (or, alternatively, a preset) criterion (e.g., 30 minutes).

In one example, the controller 120 may apply an algorithm for reducing the power consumption in consideration of the influence of the gravity in the power saving mode. For this, the sensor 110 may measure the current gait motion of the user 200. Also, the controller 120 may define a state variable based on the current gait motion and generate the torque profile based on the state variable and the gravity for a left or right leg of a descending state of a swing phase.

In another example, the controller 120 may apply an algorithm for reducing the power consumption based on a delay and a state variable in the power saving mode. The controller 120 may define a state variable based on a current gait motion, set a delay corresponding to a feedback factor for the state variable, and generate a torque profile based on the state variable and the delay. The controller 120 may adjust a gain and a delay time based on a movement of the user 200.

In the power saving mode, the walking assistance apparatus 100 may generate the torque profile based on the algorithm of the power saving mode to reduce the power consumption of the walking assistance apparatus 100. In one example, the controller 120 may set the torque profile such that a maximum intensity of torque applied to the driver 130 is less than a maximum intensity of torque applied to the driver 130 in the normal mode. When the maximum intensity of torque is reduced, an effective value of a voltage for supplying the torque may be reduced. Accordingly, the power consumption of the walking assistance apparatus 100 may be reduced.

In another example, the controller 120 may set the torque profile such that a maximum intensity of torque applied to the driver 130 to assist a leg lifting motion of the user 200 wearing the walking assistance apparatus 100 is greater than a maximum intensity of torque applied to the driver 130 to assist a leg lowering motion of the user 200. Through this, the controller 120 may perform a flexion-based gait assistance for the leg lifting motion among gait motions of the user in the power saving mode.

In another example, the controller 120 may set the torque profile based on a set (or, alternatively, a preset) torque profile associated with the power saving mode. The controller 120 may drive the driver 130 based on the set (or, alternatively, preset) torque profile. For example, the set (or, alternatively, preset) torque profile may be a torque profile set to offset a resistance force due to a friction applied by the walking assistance apparatus 100 to a movement of the user 200. According to the corresponding torque profile, a minimum torque may be applied to the driver 130.

In some example embodiments, the controller 120 may perform the aforementioned operation of the power saving mode in a stepwise manner. For example, the controller 120 may control the operation of the walking assistance apparatus 100 by slightly reducing the maximum intensity of torque in response to the operable time of the walking assistance apparatus 100 being reduced, performing the flexion-based gait assistance, and applying a minimum torque to the driver 130, in sequence. When the amount of power remaining in the battery is reduced to be insufficient to perform a function of the walking assistance apparatus 100 normally, the controller 120 may control the walking assistance apparatus 100 such that the torque applied to the walking assistance apparatus 100 is gradually reduced. Through this, the walking assistance apparatus 100 may prevent the user 200 from falling due to an abrupt power-off.

The walking assistance device 100 may include a memory 125 configured to store torque parameters corresponding to the torque profile output by the controller 120. Although FIG. 1 illustrates that the memory 125 is included in the controller 120, the memory 125 may also be located external to the controller 120.

The driver 130 may be located at left and right hip parts of the user 200 to drive both hip-joints of the user 200. The driver 130 may generate a force to assist walking of the user 200 under a control of the controller 120, for example, based on the torque profile generated from the controller 120.

The force transmitting member 150 may connect the driver 130 and the supporting member 160. The force transmitting member 150 may transmit the force received from the driver 130 to the supporting member 160. As an example, the force transmitting member 150 may be a longitudinal member such as, for example, a wire, a cable, a string, a rubber band, a spring, a belt, and a chain.

The supporting member 160 may support a target part, for example, a thigh of the user 200. The supporting member 160 may be disposed to cover at least a portion of the user 200. The supporting member 160 may exert a force on the target part of the user 200 using the force received from the force transmitting member 150.

The fixing member 170 may be attached to a part, for example, a waist of the user 200. The fixing member 170 may be in contact with at least a portion of an outer surface of the user 200. The fixing member 170 may cover along the outer surface of the user 200.

The display 140 may display a user interface (UI) for controlling a delay and/or gain so as to be viewed by the user 200. For example, the user 200 may use the UI displayed on the display 140 to control a gain related to an intensity of assistance torque and/or a delay related to an output time of an assistance torque.

The display 140 may be implemented as, for example, a touchscreen, a liquid crystal display (LCD), a thin film transistor-liquid crystal display (TFT-LCD), a liquid emitting diode (LED) display, an organic LED (OLED) display, an active matrix OLED (AMOLED) display, or a flexible display.

The walking assistance apparatus 100 may include the speaker (not shown). The walking assistance apparatus 100 may use the display 140 or the speaker to inform the user 200 of a change to the power saving mode. The walking assistance apparatus 100 may inform the user of a fact that an amount of remaining power is less than a predetermined amount through the display 140 or the speaker of the walking assistance apparatus.

In another example, the walking assistance apparatus 100 may inform a remote-control device (not shown) capable of communicating with the walking assistance apparatus 100, of the change to the power saving mode. The remote-control device may be, for example, a personal computing device, a laptop computing device, a tablet computing device, a mobile device such as a smartphone, another type of wearable device such as a smart watch, or any other electronic device.

The walking assistance apparatus 100 may provide notification that the power saving mode of the walking assistance apparatus 100 is required, to the user 200 and receive a selecting input for entering the power saving mode through a user input.

Figure 3:
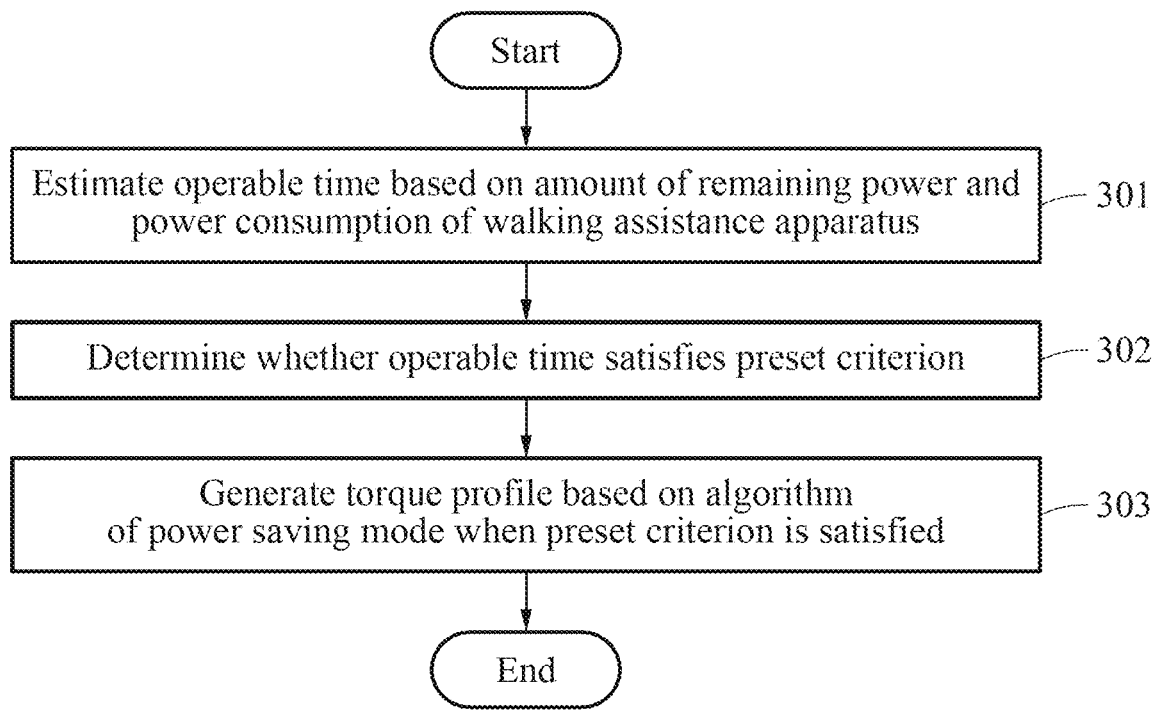
FIG. 3 is a flowchart illustrating an overall operation of a control method of a walking assistance apparatus according to at least one example embodiment.

FIG. 3 is a flowchart illustrating an overall operation of a control method of a walking assistance apparatus according to at least one example embodiment.

In operation 301, the controller 120 may estimate an operable time of the walking assistance apparatus 100 based on an amount of remaining power and power consumption of the walking assistance apparatus 100. The controller 120 may calculate an amount of power remaining in a battery. The controller 120 may estimate future power consumption of the walking assistance apparatus 100. The controller 120 may estimate an operable time from a current point in time based on the calculated amount of remaining power and the estimated power consumption.

In operation 302, the controller 120 may determine whether the operable time of the walking assistance apparatus 100 satisfies a set (or, alternatively, a preset) criterion. The controller 120 may determine whether the operable time is less than a threshold. For example, the controller 120 may determine whether the operable time is less than 30 minutes. When it is determined that the operable time of the walking assistance apparatus is less than 30 minutes, the controller 120 may determine that the amount of power remaining in the battery is insufficient and change an operation mode of the walking assistance apparatus 100 to a power saving mode to delay an assist-off time of the walking assistance apparatus 100. In this example, the controller 120 may inquire a user wearing the walking assistance apparatus 100 about whether to change to the power saving mode, or inform the user of a change to the power saving mode.

In operation 303, when the set (or, alternatively, preset) criterion is satisfied, the controller 120 may generate a torque profile based on an algorithm of the power saving mode.

In one example, the controller 120 may set the torque profile such that a maximum intensity of a torque applied to the driver 130 in the power saving mode is less than a maximum intensity of a torque applied to the driver 130 in a normal mode.

In another example, the controller 120 may set the torque profile such that a maximum intensity of a torque applied to the driver 130 to assist a leg lifting motion of a user wearing the walking assistance apparatus is greater than a maximum intensity of a torque applied to the driver to assist a leg lowering motion of the user. In this example, the walking assistance apparatus 130 may perform a gait assistance mainly for the leg lifting motion among gait motions of the user in the power saving mode.

In another example, the controller 120 set the torque profile based on a set (or, alternatively, a preset) torque profile. A preset torque profile applied in the power saving mode may exist. The controller 120 may drive the driver 130 based on the preset torque profile. For example, the preset torque profile may be a torque profile set to offset a resistance force due to a friction applied by the walking assistance apparatus 100 to a movement of the user and induce a smooth movement of the user.

In some example embodiments, the controller 120 may perform the power saving mode in a stepwise manner. For example, as the operable time of the walking assistance apparatus 100 is reduced, more intense power saving mode may be performed. The more intense power saving mode may indicate a power saving mode having less power consumption.

After the torque profile is generated, the controller 120 may drive the driver 130 of the walking assistance apparatus 100 based on the generated torque profile. Through this, an assistance force for assisting a gait motion of the user may be provided to the user.

Figure 4:
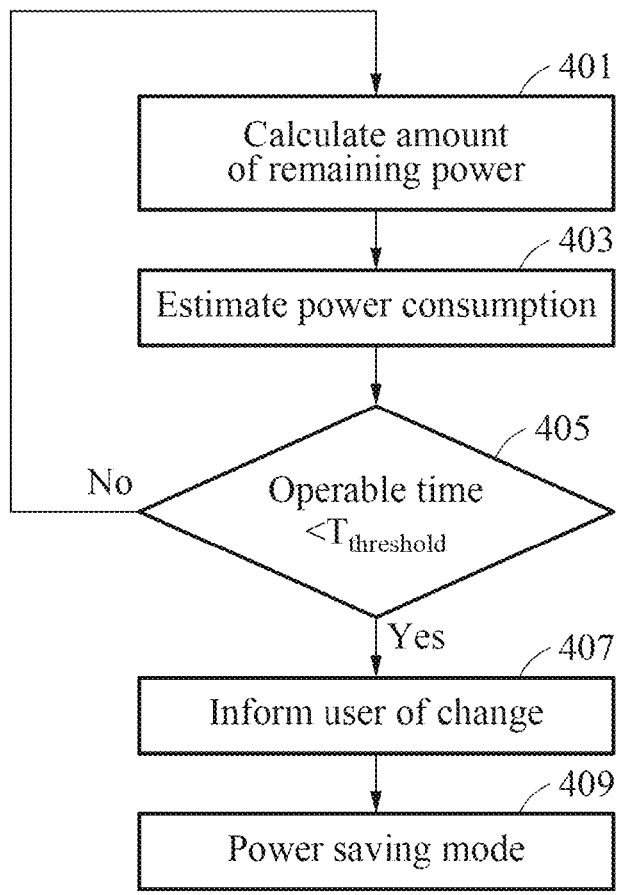
FIG. 4 is a flowchart illustrating an example of a control method of a walking assistance apparatus according to at least one example embodiment.

FIG. 4 is a flowchart illustrating an example of a control method of a walking assistance apparatus according to at least one example embodiment.

In operation 401, the controller 120 may calculate an amount of power remaining in a battery. For example, the controller 120 may determine the amount of remaining power by measuring potential of hydrogen (pH) and a proportion of electrolyte of the battery. For example, the controller 120 may determine the amount of remaining power by measuring a voltage of the battery. For example, the controller 120 may determine the amount of remaining power by using a current integral. For example, the controller 120 may determine the amount of remaining power by measuring an internal pressure of the battery. However, these are merely examples, and the controller 120 may calculate the amount of remaining power in various ways.

In operation 403, the controller 120 may estimate future power consumption of the walking assistance apparatus 100. For example, the controller 120 may estimate the power consumption based on a previous motion pattern of the user. For example, the controller 120 may estimate the power consumption based on a movement path of the user. However, these are merely examples, and the controller 120 may estimate the future power consumption in various ways.

In operation 405, the controller 120 may determine whether the operable time of the walking assistance apparatus 100 is less than a threshold. For example, the controller 120 may determine whether the operable time is less than 30 minutes. For example, the controller 120 may calculate a time taken to move to a position for charging the battery and determine whether the operable time is less than the corresponding time.

In operation 407, when the operable time of the walking assistance apparatus 100 is less than the threshold, the controller 120 may inform of a change to the power saving mode. For example, the controller 120 may use a display or a speaker to inform of the change to the power saving mode.

In operation 409, the controller 120 may perform the power saving mode. The controller 120 may perform an operation based on an algorithm of the power saving mode. For example, the controller 120 may set the torque profile such that a maximum intensity of a torque to be applied through the driver in the power saving mode is reduced. In this example, the controller 120 may set the torque profile such that the maximum intensity is reduced in an entire course of the gait motion of the user, or set the torque profile such that a maximum intensity of a torque applied to the driver to assist a leg lifting motion of the user is greater than a maximum intensity of a torque applied to the driver to assist a leg lowering motion of the user. Alternatively, the controller 120 may set the torque profile based on a set (or, alternatively, a preset) torque profile. The controller 120 may drive the driver 130 based on the set torque profile.

Figure 5:
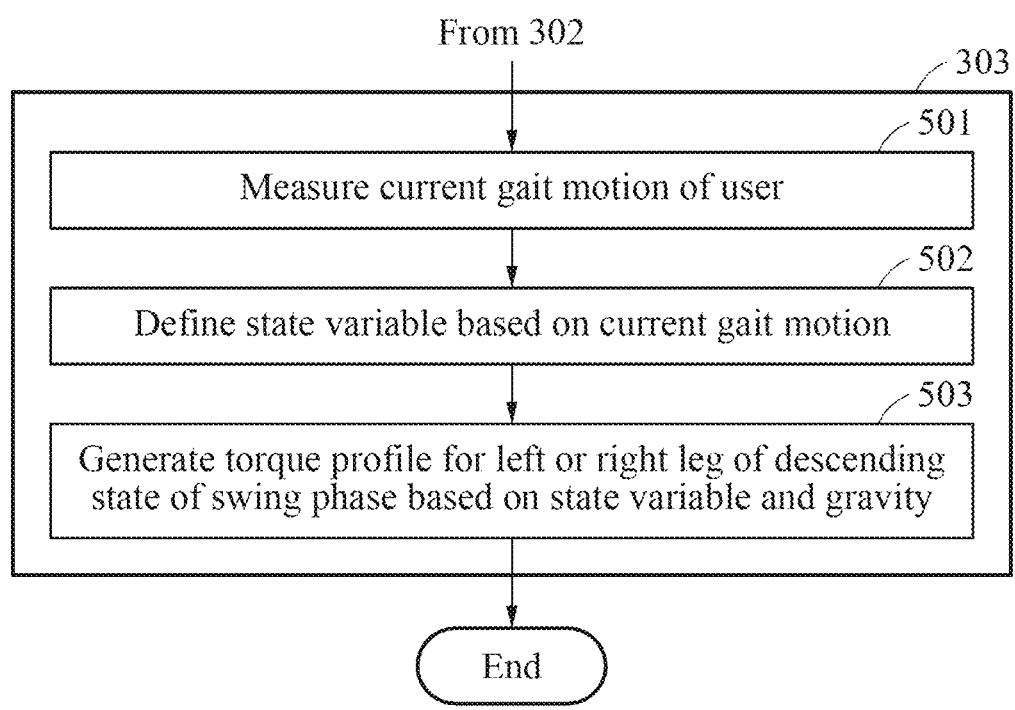
FIG. 5 is a flowchart illustrating an example of generating a torque profile in the control method of the walking assistance apparatus of FIG. 3 according to at least one example embodiment.

FIG. 5 is a flowchart illustrating an example of generating a torque profile in the control method of the walking assistance apparatus of FIG. 3 according to at least one example embodiment.

Referring to FIG. 5, in operation 303, the controller 120 may generate a torque profile based on an algorithm of a power saving mode when a set (or, alternatively, a preset) criterion is satisfied. The controller 120 may apply an algorithm of reducing power consumption in consideration of an influence of the gravity in the power saving mode. The controller 120 may generate the torque profile based on a state variable and the gravity. Operation 303 may include operations 501 to 503.

In operation 501, the controller 120 may measure a current gait motion of the user 200. In operation 502, the controller 120 may define a state variable based on the current gait motion. The controller 120 may define a state variable based on the current gait motion of the user 200 received from the sensor 110, which may also be expressed as that the controller 120 defines a state variable by receiving a feedback about the current gait motion of the user 200.

In operation 503, the controller 120 may generate the torque profile for a left or right leg of a descending state of a swing phase based on the state variable and the gravity. The controller 120 may generate the torque profile compensating for a result obtained by correcting a frictional force of the left leg or right leg of the descending state of the swing phase based on the gravity.

Figure 6:
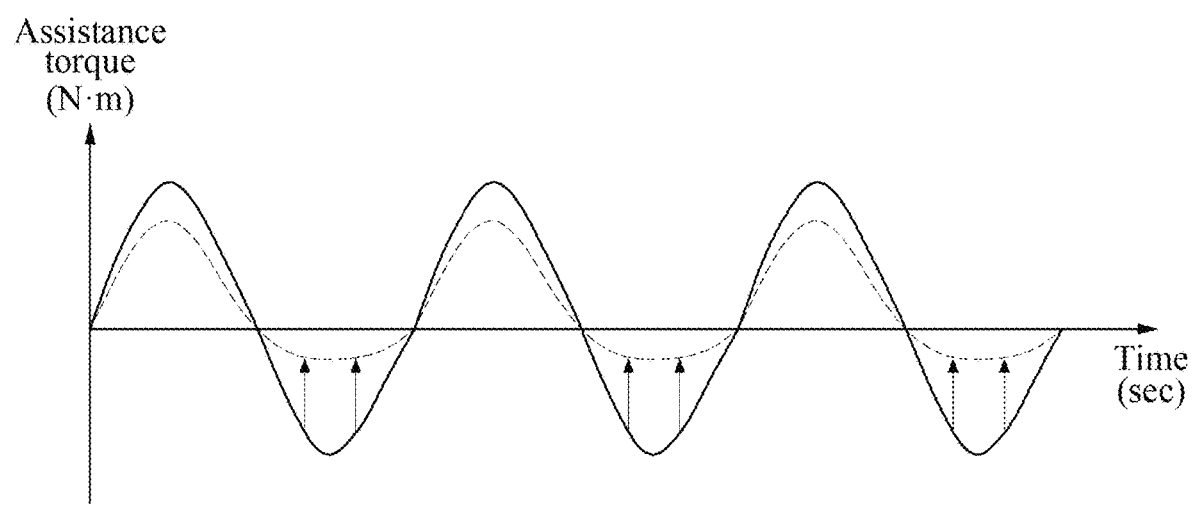
FIG. 6 is a diagram illustrating a graph of a torque profile according to at least one example embodiment.

FIG. 6 is a diagram illustrating a graph of a torque profile according to at least one example embodiment.

Referring to FIG. 6, an upper portion above a horizontal axis represents an ascending state of a leg over time and a lower portion below the horizontal axis represents a descending state of the leg over time. The controller 120 may reduce the assistance torque in the descending state using the gravity. In some cases, the walking assistance apparatus may generate an assistance torque for a frictional force that is not removed by the gravity. Through this, the walking assistance apparatus may realize minimum power in the descending state.

As illustrated in FIG. 6, in the power saving mode, a torque profile may be set such that a maximum intensity of a torque applied to the driver 130 to assist a leg lifting motion of a user wearing the walking assistance apparatus 100 is greater than a maximum intensity of a torque applied to the driver 130 to assist a leg lowering motion of the user. In this case, the walking assistance apparatus 100 may perform a gait assistance mainly for the leg lifting motion among gait motions of the user in the power saving mode.

Figure 7:
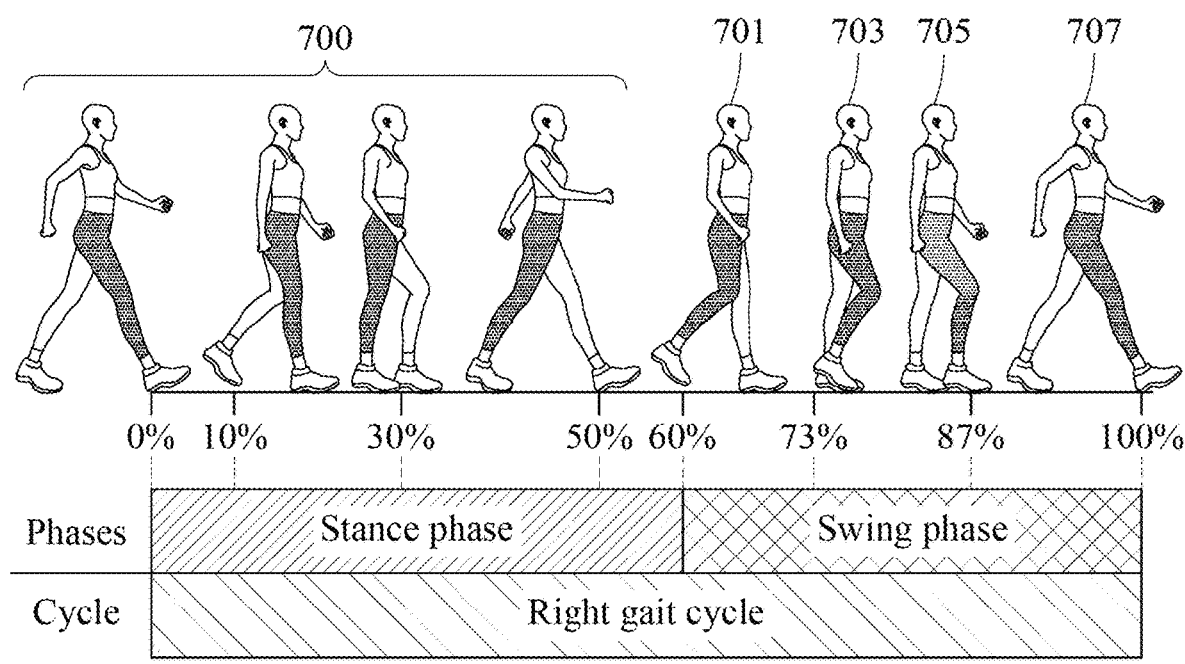
FIG. 7 is a diagram illustrating a gait cycle to which the control method of the walking assistance apparatus of FIG. 5 is applied according to at least one example embodiment.

FIG. 7 is a diagram illustrating a gait cycle to which the control method of the walking assistance apparatus of FIG. 5 is applied according to at least one example embodiment.

Referring to FIG. 7, FIG. 7 illustrates a gait cycle of a right leg and the following description may be equally applied to a left leg. In a human gait cycle, based on a leg on one side, a stance phase 700 in which a leg is in contact with a ground and a swing phase in which the leg is not in contact with the ground are alternated. The swing phase may be divided into gait states 701 and 703 corresponding to an ascending state in which the right leg moves in a direction opposite to the gravity, and gait states 705 and 707 corresponding to a descending state in which the right leg moves in the same direction as the gravity. Specifically, the ascending state and the descending state may be distinguished based on a time at which the right leg is at a highest position between the gait state 703 and the gait state 705.

Figure 8:
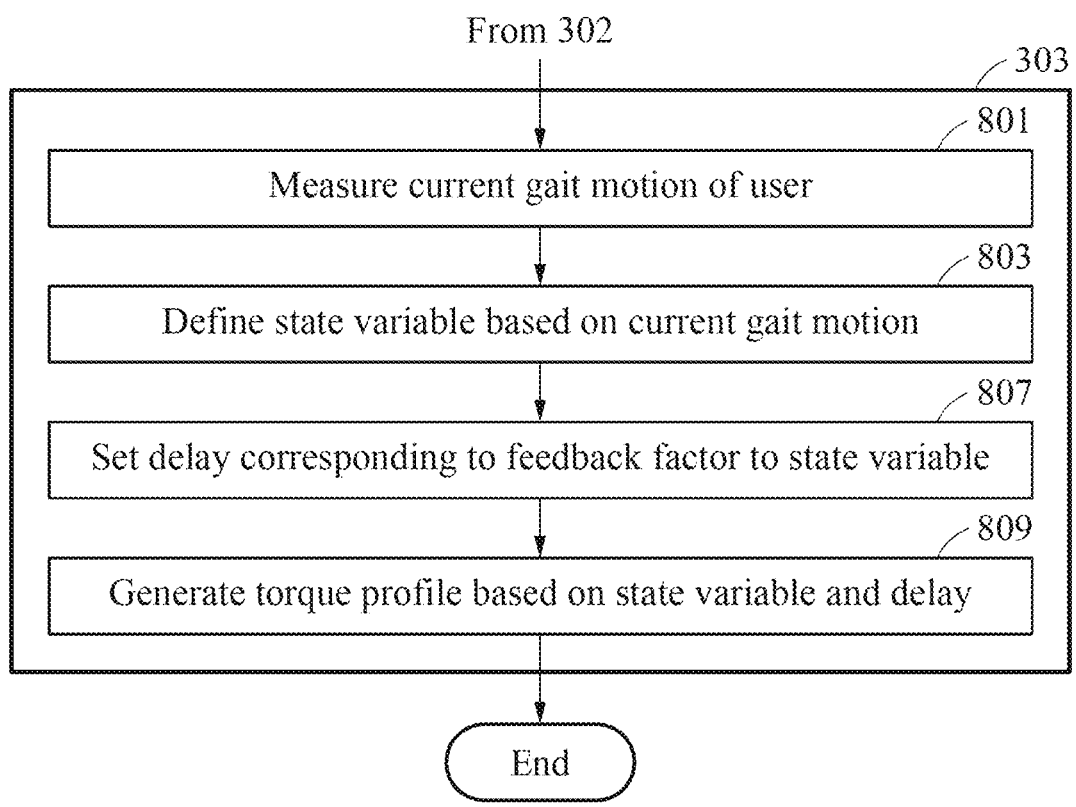
FIG. 8 is a flowchart illustrating another example of generating a torque profile in the control method of the walking assistance apparatus of FIG. 3 according to at least one example embodiment.

FIG. 8 is a flowchart illustrating another example of generating a torque profile in the control method of the walking assistance apparatus of FIG. 3 according to at least one example embodiment.

Referring to FIG. 8, in operation 303, the controller 120 may generate a torque profile based on an algorithm of a power saving mode when a set (or, alternatively, a preset) criterion is satisfied. The controller 120 may generate the torque profile based on a state variable in the power saving mode and a delay corresponding to a feedback factor for the state variable. Operation 303 may include operations 801 to 809.

In operation 801, the controller 120 may measure a current gait motion of a user. The controller 120 may measure a gait speed of the user based on the current gait motion of the user received from the sensor 110. The controller 120 may measure a gait acceleration of the user based on the current gait motion of the user received from the sensor 110. The controller 120 may measure the gait acceleration based on hip-joint angular velocity information.

In operation 803, the controller 120 may define a state variable based on the current gait motion. In operation 807, the controller 120 may set a delay corresponding to a feedback factor to the state variable. In operation 809, the controller 120 may generate a torque profile based on the state variable and the delay.

The controller 120 may define the state variable by setting a gain related to an intensity of torque and a delay related to a torque output time. The controller 120 may control an intensity of an assistance torque applied to the user based on the gain and control a time of the assistance torque applied to the user based on the delay.

For example, the controller 120 may determine the delay based on the gait speed of the user. The controller 120 may set a relatively short delay when the gait speed of the user is greater than a first reference value and set a relatively long delay when the gait speed of the user is less than the first reference value.

Also, the controller 120 may determine the delay based on the gait acceleration of the user. The controller 120 may set a relatively short delay when the gait acceleration of the user is greater than a second reference value and set a relatively long delay when the gait acceleration of the user is less than the second reference value.

Figure 9:
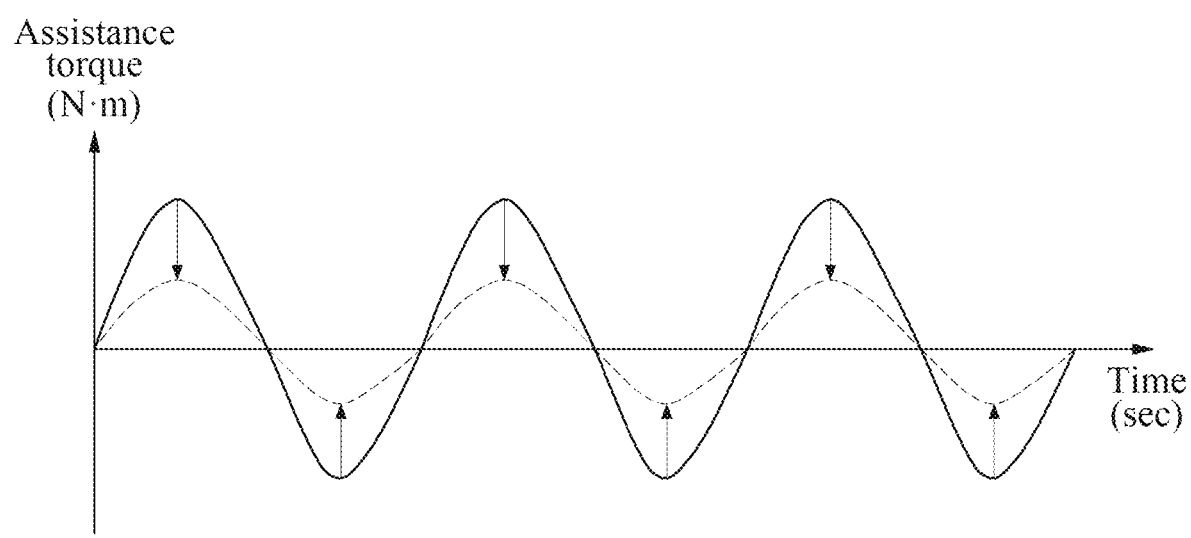
FIG. 9 is a diagram illustrating a graph of a torque profile according to at least one example embodiment.

FIG. 9 is a diagram illustrating a graph of a torque profile according to at least one example embodiment.

Referring to FIG. 9, an upper portion above a horizontal axis represents an ascending state of a leg over time and a lower portion below a horizontal axis represents a descending state of the leg over time.

As illustrated in FIG. 9, a torque profile may be set such that a maximum intensity of a torque applied to a driver 130 in a power saving mode is less than a maximum intensity of a torque applied to the driver in a normal mode. Also, a torque profile of the walking assistance apparatus 100 may be set based on a set (or, alternatively, a preset) torque profile such that a torque of a reduced (or, alternatively, a minimum) intensity is supplied through the driver 130 in the power saving mode. For example, the set or (alternatively, preset) torque profile may be a torque profile set to supply a torque of an intensity at which a resistance force due to a friction applied by the walking assistance apparatus to a movement of the user is offset.

The units and/or modules described herein may be implemented using hardware components and software components. For example, the hardware components may include microphones, amplifiers, band-pass filters, audio to digital convertors, and processing devices. A processing device may be implemented using one or more hardware device configured to carry out and/or execute program code by performing arithmetical, logical, and input/output operations. The processing device(s) may include a processor, a controller and an arithmetic logic unit, a digital signal processor, a microcomputer, a field programmable array, a programmable logic unit, a microprocessor or any other device capable of responding to and executing instructions in a defined manner. The processing device may run an operating system (OS) and one or more software applications that run on the OS. The processing device also may access, store, manipulate, process, and create data in response to execution of the software. For purpose of simplicity, the description of a processing device is used as singular; however, one skilled in the art will appreciated that a processing device may include multiple processing elements and multiple types of processing elements. For example, a processing device may include multiple processors or a processor and a controller. In addition, different processing configurations are possible, such as parallel processors.

The software may include a computer program, a piece of code, an instruction, or some combination thereof, to independently or collectively instruct and/or configure the processing device to operate as desired, thereby transforming the processing device into a special purpose processor. Software and data may be embodied permanently or temporarily in any type of machine, component, physical or virtual equipment, computer storage medium or device, or in a propagated signal wave capable of providing instructions or data to or being interpreted by the processing device. The software also may be distributed over network coupled computer systems so that the software is stored and executed in a distributed fashion. The software and data may be stored by one or more non-transitory computer readable recording mediums.

The methods according to the above-described example embodiments may be recorded in non-transitory computer-readable media including program instructions to implement various operations of the above-described example embodiments. The media may also include, alone or in combination with the program instructions, data files, data structures, and the like. The program instructions recorded on the media may be those specially designed and constructed for the purposes of example embodiments, or they may be of the kind well-known and available to those having skill in the computer software arts. Examples of non-transitory computer-readable media include magnetic media such as hard disks, floppy disks, and magnetic tape; optical media such as CD-ROM discs, DVDs, and/or Blue-ray discs; magneto-optical media such as optical discs; and hardware devices that are specially configured to store and perform program instructions, such as read-only memory (ROM), random access memory (RAM), flash memory (e.g., USB flash drives, memory cards, memory sticks, etc.), and the like. Examples of program instructions include both machine code, such as produced by a compiler, and files containing higher level code that may be executed by the computer using an interpreter. The above-described devices may be configured to act as one or more software modules in order to perform the operations of the above-described example embodiments, or vice versa.

A number of example embodiments have been described above. Nevertheless, it should be understood that various modifications may be made to these example embodiments. For example, suitable results may be achieved if the described techniques are performed in a different order and/or if components in a described system, architecture, device, or circuit are combined in a different manner and/or replaced or supplemented by other components or their equivalents. Accordingly, other implementations are within the scope of the following claims.

What is claimed is:

1. A control method of a walking assistance apparatus, the method comprising:
    estimating an operable time of the walking assistance apparatus based on an amount of remaining power and a power consumption of the walking assistance apparatus; and
    generating a torque profile based on an algorithm of a power saving mode in response to the operable time satisfying a set criterion.

2. The control method of claim 1, wherein the generating of the torque profile comprises:
    setting the torque profile such that a maximum intensity of a torque applied to a driver of the walking assistance apparatus in the power saving mode is less than a maximum intensity of a torque applied to the driver in a normal mode.

3. The control method of claim 2, wherein the generating of the torque profile comprises:
    setting the torque profile based on a set torque profile associated with the power saving mode.

4. The control method of claim 1, wherein the generating of the torque profile comprises:
    setting, in the power saving mode, the torque profile such that a maximum intensity of a torque applied to a driver of the walking assistance apparatus to assist a leg lifting motion of a user wearing the walking assistance apparatus is greater than a maximum intensity of a torque applied to the driver to assist a leg lowering motion of the user.

5. The control method of claim 1, wherein the estimating of the operable time comprises:
    calculating the amount of remaining power; and
    estimating the power consumption.

6. The control method of claim 1, wherein the generating of the torque profile comprises:
    measuring a current gait motion of a user;
    defining a state variable based on the current gait motion; and
    generating, based on the state variable and a gravity, the torque profile for a descending state of a swing phase of one or more of a left leg or right leg of the user.

7. The control method of claim 6, wherein the generating of the torque profile comprises:
    generating the torque profile such that the torque profile compensates for a frictional force of the left leg or the right leg of the descending state of the swing phase based on the gravity.

8. The control method of claim 1, further comprising:
    informing a user wearing the walking assistance apparatus of a change to the power saving mode in response to the set criterion being satisfied.

9. The control method of claim 8, wherein the informing comprises:
    informing the user of the change to the power saving mode through a display or a speaker.

10. The control method of claim 1, further comprising:
    driving a driver of the walking assistance apparatus based on the torque profile.

11. A non-transitory computer-readable medium comprising computer readable instructions that, when executed, cause a computer to perform the control method of claim 1.

12. A walking assistance apparatus comprising:
    a sensor configured to measure a gait motion of a user wearing the walking assistance apparatus; and
    a controller configured to,
        estimate an operable time of the walking assistance apparatus based on an amount of remaining power and power consumption of the walking assistance apparatus, and
        generate a torque profile based on an algorithm of a power saving mode in response to the operable time satisfying a set criterion.

13. The walking assistance apparatus of claim 12, wherein the controller is configured to set the torque profile such that a maximum intensity of a torque applied to a driver in the power saving mode is less than a maximum intensity of a torque applied to the driver in a normal mode.

14. The walking assistance apparatus of claim 13, wherein the controller is configured to set the torque profile based on a set torque profile associated with the power saving mode.

15. The walking assistance apparatus of claim 12, wherein the controller is configured to set, in the power saving mode, the torque profile such that a maximum intensity of a torque applied to a driver to assist a leg lifting motion of the user is greater than a maximum intensity of a torque applied to the driver to assist a leg lowering motion of the user.

16. The walking assistance apparatus of claim 12, further comprising:
   at least one of a display and a speaker configured to inform the user of a change to the power saving mode when the operable time satisfies the set criterion.

17. The walking assistance apparatus of claim 12, further comprising:
   a driver configured to drive a support of the walking assistance apparatus based on the torque profile to assist the gait motion of the user.

* * * * *